United States Patent
Twede et al.

(10) Patent No.: US 10,371,625 B1
(45) Date of Patent: Aug. 6, 2019

(54) IDENTIFICATION OF A REFLECTIVE SURFACE AS BEING ASSOCIATED WITH A THREAT OPTIC

(71) Applicant: Lockheed Martin Corporation, Bethesda, MD (US)

(72) Inventors: David R. Twede, Orlando, FL (US); Suresh Subramanian, Orlando, FL (US); Richard William Guthrie, Orlando, FL (US)

(73) Assignee: Lockheed Martin Corporation, Bethesda, MD (US)

( * ) Notice: Subject to any disclaimer, the term of this patent is extended or adjusted under 35 U.S.C. 154(b) by 175 days.

(21) Appl. No.: 15/190,633

(22) Filed: Jun. 23, 2016

Related U.S. Application Data

(60) Provisional application No. 62/183,338, filed on Jun. 23, 2015.

(51) Int. Cl.
*G01N 21/21* (2006.01)
*G01N 21/17* (2006.01)

(52) U.S. Cl.
CPC ..... *G01N 21/21* (2013.01); *G01N 2021/1748* (2013.01); *G01N 2021/216* (2013.01); *G01N 2201/06113* (2013.01); *G01N 2201/12* (2013.01)

(58) Field of Classification Search
CPC ............................. H04N 13/0434; G01S 17/74
USPC ........................................................ 348/135
See application file for complete search history.

(56) References Cited

U.S. PATENT DOCUMENTS

| | | | | |
|---|---|---|---|---|
| 5,418,810 A | * | 5/1995 | Eguchi | G02F 1/37 372/107 |
| 5,537,209 A | * | 7/1996 | Lis | G01B 9/02007 356/487 |
| 5,585,921 A | * | 12/1996 | Pepper | G01N 29/075 356/432 |
| 6,069,565 A | * | 5/2000 | Stern | B64D 15/20 340/583 |
| 6,181,430 B1 | * | 1/2001 | Meyer | G01B 9/02007 356/495 |
| 6,256,283 B1 | * | 7/2001 | Fukakusa | G11B 7/127 369/112.01 |
| 6,556,533 B1 | * | 4/2003 | Fukakusa | G11B 7/1275 369/112.17 |
| 8,010,316 B2 | * | 8/2011 | Maltseff | G01S 17/36 356/5.05 |
| 8,731,240 B1 | | 5/2014 | Woodman et al. | |
| 9,482,617 B2 | * | 11/2016 | Smith | G01N 21/6486 |

(Continued)

*Primary Examiner* — Paulos M Natnael
(74) *Attorney, Agent, or Firm* — Withrow & Terranova, PLLC

(57) ABSTRACT

Identification of reflective surfaces as being associated with optical threats is disclosed. A first laser signal is emitted from a first laser system at a first wavelength and a first emission circular polarization orientation. A first signal reflection of the first laser signal from a reflective surface at the first wavelength having a first return circular polarization orientation that is different from the first emission circular polarization orientation is detected. A first return quantification of the first signal reflection, based at least in part on an amount of circular polarization of the first signal reflection, is determined. It is determined that the reflective surface is associated with a threat optic based at least in part on the first return quantification.

21 Claims, 6 Drawing Sheets

(56) References Cited

U.S. PATENT DOCUMENTS

| | | | |
|---|---|---|---|
| 2003/0231315 A1* | 12/2003 | Arbore | G01M 11/331 356/477 |
| 2006/0065820 A1* | 3/2006 | Nagai | G01R 33/032 250/225 |
| 2006/0072118 A1* | 4/2006 | Chan | A61B 5/0066 356/495 |
| 2006/0158734 A1* | 7/2006 | Schuurmans | G01J 3/02 359/487.04 |
| 2008/0068959 A1* | 3/2008 | Saito | G11B 7/0956 369/53.19 |
| 2008/0316026 A1* | 12/2008 | Yenisch | G01S 7/4815 340/555 |
| 2010/0253769 A1* | 10/2010 | Coppeta | G02B 27/1026 348/58 |
| 2015/0355327 A1* | 12/2015 | Goodwin | G01S 17/325 356/5.01 |

* cited by examiner

IDENTIFICATION OF A REFLECTIVE SURFACE AS BEING ASSOCIATED WITH A THREAT OPTIC

RELATED APPLICATIONS

This application claims the benefit of provisional patent application No. 62/183,338, filed on Jun. 23, 2015, entitled "MULTIMODAL DETECTION OF OPTICAL DEVICES," the disclosure of which is hereby incorporated herein by reference in its entirety.

TECHNICAL FIELD

The embodiments relate generally to identifying a reflective surface in a scene as being associated with a threat optic.

BACKGROUND

In many circumstances it would be useful to determine if a device that utilizes ultraviolet wavelengths, visible wavelengths, or infrared wavelengths, such as a sniper scope, a pair of binoculars, field glasses, monoculars, a digital camera, a video recorder, a sight of a weapon, or the like, referred to herein as a "threat optic," is surveilling a location. Reflections from manmade surfaces can sometimes be detected by a camera, but not all manmade surfaces constitute a threat. Thus, distinguishing reflections from a potentially dangerous object, such as a threat optic, and reflections from background clutter reflectors, such as bottles, cans, headlights, and other reflective surfaces, would be useful.

SUMMARY

The embodiments relate to systems and methods for characterizing a reflective surface in a scene as being associated with a threat optic to distinguish a reflective surface associated with a potentially dangerous object from reflective surfaces of non-threatening objects.

In one embodiment a method for identifying a threat optic in a scene is provided. A first laser signal is emitted from a first laser system at a first wavelength and a first emission circular polarization orientation. A first signal reflection of the first laser signal from a reflective surface at the first wavelength having a first return circular polarization orientation that is different from the first emission circular polarization orientation is detected. A first return quantification of the first signal reflection based at least in part on an amount of circular polarization of the first signal reflection is determined. It is determined that the reflective surface is associated with a threat optic based at least in part on the first return quantification.

In one embodiment determining the first return quantification based at least in part on the amount of circular polarization of the first signal reflection includes passing the first signal reflection through a ¼ wave plate to convert the first signal reflection into linearly polarized light. The linearly polarized light is passed through four polarizers oriented at four different orientation positions. A ratio of light received at the four different orientation positions is determined. The amount of circular polarization of the first signal reflection is determined based on the ratio.

In one embodiment the four different orientation positions comprise a 0 degree position, a 45 degree position, a 90 degree position, and a 135 degree position.

In another embodiment the composition of the threat optic may be identified. A second laser signal is emitted from a second laser system at a second wavelength and a second emission circular polarization orientation. The second wavelength is different from the first wavelength, or the second emission circular polarization orientation is different from the first emission circular polarization orientation. A second signal reflection of the second laser signal from the reflective surface at the second wavelength having a second return circular polarization orientation that is different from the second emission circular polarization orientation is detected. A second return quantification of the second signal reflection based at least in part on an amount of circular polarization of the second signal reflection is determined. A composition of the threat optic is determined based at least in part on a comparison of the first return quantification to the second return quantification.

Those skilled in the art will appreciate the scope of the disclosure and realize additional aspects thereof after reading the following detailed description of the preferred embodiments in association with the accompanying drawing figures.

BRIEF DESCRIPTION OF THE DRAWINGS

The accompanying drawing figures incorporated in and forming a part of this specification illustrate several aspects of the disclosure and, together with the description, serve to explain the principles of the disclosure.

DETAILED DESCRIPTION

The embodiments set forth below represent the necessary information to enable those skilled in the art to practice the embodiments and illustrate the best mode of practicing the embodiments. Upon reading the following description in light of the accompanying drawing figures, those skilled in the art will understand the concepts of the disclosure and will recognize applications of these concepts not particularly addressed herein. It should be understood that these concepts and applications fall within the scope of the disclosure and the accompanying claims.

Any flowcharts discussed herein are necessarily discussed in some sequence for purposes of illustration, but unless otherwise explicitly indicated, the embodiments are not limited to any particular sequence of steps. The use herein of ordinals in conjunction with an element is solely for distinguishing what might otherwise be similar or identical labels, such as "first laser signal" and "second laser signal," and does not imply a priority, a type, an importance, or other attribute, unless otherwise stated herein. The phrase "light" as used herein refers to electromagnetic radiation in the infrared, visible, and ultraviolet spectrums.

As used herein and in the claims, the articles "a" and "an" in reference to an element refers to "one or more" of the element unless otherwise explicitly specified.

The embodiments relate to systems and methods for characterizing a reflective surface in a scene as a threat optic to distinguish a potentially dangerous reflective surface from non-dangerous reflective surfaces. Threat optics are characterized by an amount of circular polarization retained in the light reflected from the threat optic. The reflected light may be reflected from an optical element of the threat optic, such as a lens, or from a relatively planar surface of the threat optic, such as a focal plane array, a reticle, or other linear detector array. Threat optics typically have a focusing lens arrangement that focuses light received by the device to a focal plane, a linear detector array, or a reticle. Examples of threat optics include, by way of non-limiting example, sniper scopes, binoculars, field glasses, a sight of a weapon, monoculars, digital cameras, and video recorders.

Figure 1:
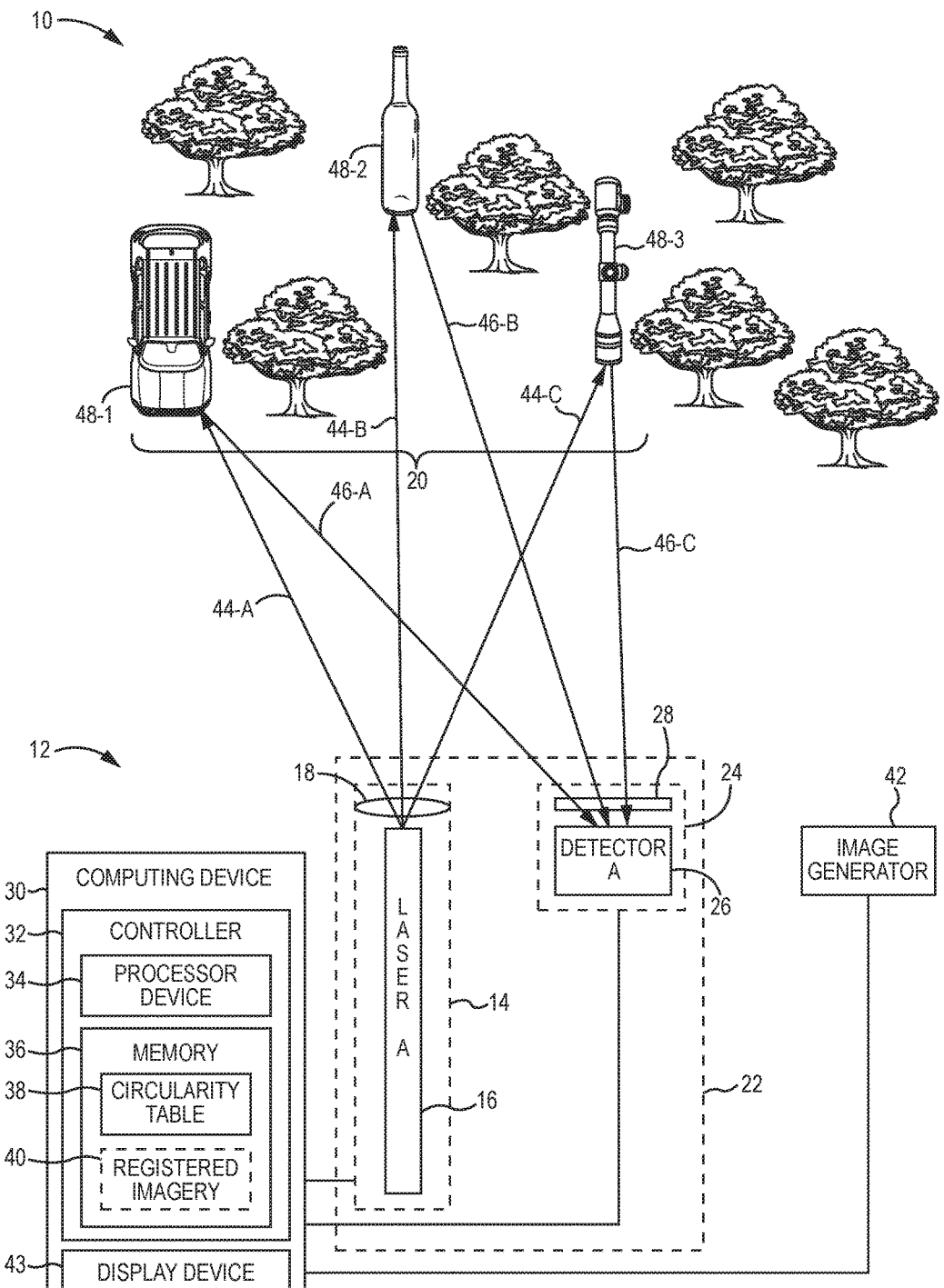
FIG. 1 is a block diagram of an environment in which embodiments may be practiced.

FIG. 1 is a diagram of an environment 10 in which embodiments may be practiced. The environment 10 includes a system 12 according to one embodiment. The system 12 includes a first laser system 14 that includes a first laser transmitter 16 and, in this embodiment, an optical element 18, such as a right hand quarter wave plate that right hand circularly polarizes laser signals emitted from the first laser transmitter 16. The first laser transmitter 16 may emit laser signals in any desired wavelengths, including, by way of non-limiting example, in the infrared, visible, or ultraviolet wavelengths. The first laser system 14 has a field of regard within which a scene 20 exists. In this example, the scene 20 includes trees and various reflective surfaces, as will be discussed in greater detail below.

The field of regard of the first laser system 14 is based on an amount of horizontal and vertical scanning of the first laser system 14. In one embodiment, the first laser system 14 may be mounted to a turntable 22 that is configured to rotate a pointing direction of the first laser system 14 horizontally within a desired arc. In some embodiments, the turntable 22 is capable of rotating the pointing direction of the first laser system 14 360 degrees. The first laser system 14 may also be able to scan laser signals vertically. Thus, in one embodiment, the first laser system 14 emits a laser signal that is scanned both horizontally and vertically within the scene 20.

The system 12 includes a first detection system 24 that includes a first detector 26 sensitive to laser signals in the same wavelength as the laser signal emitted by the first laser transmitter 16. In this embodiment, the first detection system 24 also includes a left hand circular polarizer filter arrangement 28 that filters out light that has a polarization orientation other than a left hand circular polarization orientation. In other words, the left hand circular polarizer filter arrangement 28 passes left hand circularly polarized light to the first detector 26 and blocks all other light. The first detection system 24 may also include a wavelength filter that blocks wavelengths other than the wavelength of the laser signal emitted by the first laser transmitter 16.

The system 12 includes a computing device 30 that includes a controller 32 that includes a processor device 34 and a memory 36. The memory 36 includes a circularity table 38, the contents of which will be discussed below. In some embodiments, certain functionality described herein may be implemented as a computer program product stored on a transitory or non-transitory computer-usable or computer-readable storage medium, which includes complex programming instructions, such as complex computer-readable program code, configured to cause the controller 32 to carry out the steps described herein.

All or a portion of the embodiments may be implemented as a computer program product stored on a transitory or non-transitory computer-usable or computer-readable storage medium, which includes complex programming instructions, such as complex computer-readable program code, configured to cause the processor device 34, or the controller 32 to carry out the steps described herein.

The computing device 30 may also include registered imagery 40 of the scene 20. The registered imagery 40 is registered with the first laser system 14 such that the location of objects, such as optical elements, detected by the system 12 can be identified with respect to the registered imagery 40. Alternatively or supplementally, the system 12 may include an image generator 42. The image generator 42 comprises an image generation system capable of generating real-time imagery of the scene 20. The image generator 42 may comprise, for example, a video camera or a laser illumination and imaging system. The image generator 42 is co-aligned and registered with the first laser system 14 such that the location of objects, such as optical elements, detected by the system 12 can be identified with respect to imagery generated by the image generator 42 and displayed, for example, on a display device 43.

In operation, the first laser system 14 emits laser signals 44-A-44-C (generally, "laser signals 44") at a first wavelength and at a first circular polarization orientation, such as a right hand circular polarization orientation or a left hand circular polarization orientation, into the scene 20. The first laser system 14 is directed in a particular direction of the scene 20, and the first detection system 24 may be co-aligned with the first laser system 14 such that the first detection system 24 is pointed in a same direction as the first laser system 14 and receives signal reflections 46-A-46-C (generally, "signal reflections 46") from reflective objects 48-1-48-3 (generally, "reflective objects 48") that are within the immediate field of view of a specific laser signal 44. As discussed above, the first laser system 14 and the first detection system 24 may be scanned both vertically and horizontally to encompass the entire scene 20, such as at a rate of ¼ Hertz to 1 Hertz, for example. The first laser system 14 may emit a pulsed laser signal 44, and the first detection system 24 may be time-gated to receive the signal reflection 46 of each pulsed laser signal 44. The computing device 30 may also identify a range to a particular reflective surface based on a round trip time of a laser signal pulse from the first laser system 14 to the first detection system 24. The system 12 may also keep track of the precise direction of the laser signal 44 at any given time in terms of, by way of non-limiting example, elevation and azimuth, such that a reflective surface may be identified in terms of range and location in terms of elevation and azimuth.

The first detection system 24 may filter out light having the same circular polarization orientation as the emitted laser signal 44, but pass light having the opposite circular polarization orientation. For example, if the laser signal 44 has a right hand circular polarization orientation, the first detection system 24 may filter out light having a right hand circular polarization orientation and pass light having a left hand circular polarization orientation. This is because circularly polarized light that reflects off a planar surface, such as a reticle, a focal plane array, a charge-coupled device (CCD)/complimentary metal-oxide semiconductor (CMOS) sensor, or other planar surface, remains circularly polarized, but has the opposite handedness than that of the original laser signal. Circularly polarized light that reflects off of other reflective surfaces typically will not retain such circular polarization. Thus, an amount of circular polarization retained in a signal reflection can be a basis for determining the type of device that caused the signal reflection. Moreover, a threat optic often has an optical axis that light entering, and leaving, travels along, due to the optical and columnar structure of the threat optic. Thus, light emitted by the first laser system 14 and subsequently detected by the first detection system 24 that has retained its purely circular polarization can be indicative of an exact 180 degree reflection, and an amount or quantity of such circularly polarized light can be indicative of a threat optic.

The computing device 30 determines an amount of circular polarization of the signal reflection 46 and, based at least in part on the amount of circular polarization, determines a return quantification of the signal reflection 46. Based on the return quantification of the signal reflection 46, the computing device 30 determines whether a reflective surface is associated with a threat optic. In one embodiment, the computing device 30 may access the circularity table 38 which, in part based on the return quantification of the signal reflection 46, provides data that provides threshold information regarding amounts of circular polarization and corresponding threat optics.

While for purposes of illustration the embodiments refer to the circularity table 38, the return quantification may be determined in any of a number of different ways. In one embodiment, Mueller Matrix calculations to model the circularity of the signal reflections 46 may be performed. For example, to analyze circular polarization orientations, a ¼ waveplate can be used to rotate received signal reflections 46 into linearly polarized light. The system 12 can analyze the circularity of the signal reflections 46 using any desired number of linear polarizers, such as 2, 4, or 8 to obtain a desired number of Stokes matrix terms. Solely for purposes of illustration, the embodiments will be discussed in conjunction with four linear polarizers. Table 1 below outlines a normalized polarization orientation return signal based on four sensing linear polarizers rotated at 0 degrees, 45 degrees, 90 degrees and 135 degrees (relative to each other). The top row of Table 1 identifies potential incoming polarization orientations before passing through the ¼ waveplate, with "Horizontal" and "Vertical" denoting linear polarization orientations at 0 degrees and 90 degrees respectively, with "R-CP" and "L-CP" denoting right hand circular and left hand circular polarization orientations respectively, "+45" and "−45" denoting linear polarization orientations at 45 degrees from horizontal and 45 degrees from vertical (or 135 degrees), and "Unpolarized" denoting random polarization orientations. The first column identifies the sensor polarization rotations from 0-135 degrees. In Table 1, a value of 0 denotes no relative signal; a value of 1 denotes peak relative signal; and a value of 0.5 denotes half relative signal. For most applications, the contrast between peak relative signal and no relative signal will best indicate the polarization orientation of the incoming signal.

TABLE 1

(Quarter Waveplate Model on Receiving Device)

|  | Horizontal | Vertical | R-CP | L-CP | +45 | −45 | Unpolarized |
|---|---|---|---|---|---|---|---|
| Pol-0 | 0.5 | 0.5 | 0 | 1 | 0.5 | 0.5 | 0.5 |
| Pol-45 | 0 | 1 | 0.5 | 0.5 | 0.5 | 0.5 | 0.5 |
| Pol-90 | 0.5 | 0.5 | 1 | 0 | 0.5 | 0.5 | 0.5 |
| Pol-135 | 1 | 0 | 0.5 | 0.5 | 0.5 | 0.5 | 0.5 |

Table 2 below similarly outlines the normalized polarization return signal based only on linear polarization. In this example, the incoming signal is not passed through a ¼ waveplate and is not translated into any other state. The incoming signal is directly analyzed by the four polarization rotations from 0-135 degrees (the first column of Table 2).

TABLE 2

(Linear Polarization Model on Receiving Device)

|  | Horizontal | Vertical | R-CP | L-CP | +45 | −45 | Unpolarized |
|---|---|---|---|---|---|---|---|
| Pol-0 | 1 | 0 | 0.5 | 0.5 | 0.5 | 0.5 | 0.5 |
| Pol-45 | 0.5 | 0.5 | 0.5 | 0.5 | 1 | 0 | 0.5 |
| Pol-90 | 0 | 1 | 0.5 | 0.5 | 0.5 | 0.5 | 0.5 |
| Pol-135 | 0.5 | 0.5 | 0.5 | 0.5 | 0 | 1 | 0.5 |

Table 3 below outlines an example of a system 12 that uses two detections with ¼ waveplates (denoted by WP in the first column) as in Table 1, and two linear polarizers only (denoted by L in the first column) as in Table 2. With this mixture or with other mixtures of similar combinations, the system 12 may be optimized for any desired combination of incoming signals.

TABLE 3

(Combination of 4 from Tables 1 and 2)

|  | Horizontal | Vertical | R-CP | L-CP | +45 | −45 | Unpolarized |
|---|---|---|---|---|---|---|---|
| WP-Pol-0 | 0.5 | 0.5 | 0 | 1 | 0.5 | 0.5 | 0.5 |
| L-Pol-90 | 0 | 1 | 0.5 | 0.5 | 0.5 | 0.5 | 0.5 |
| WP-Pol-90 | 0.5 | 0.5 | 1 | 0 | 0.5 | 0.5 | 0.5 |
| L-Pol-135 | 0.5 | 0.5 | 0.5 | 0.5 | 0 | 1 | 0.5 |

The embodiments are not limited to four polarization or a combination of four polarizations and waveplates for analysis. For example, the embodiments may utilize four linear and two to four ¼ waveplate sensing states for complete analysis of all linear and circular polarizations.

While the embodiments are illustrated in terms of circularly polarized light, the embodiments are not limited to circularly polarized light and may use linearly polarized light in some applications. If linearly polarized light is emitted by the first laser transmitter 16, then receipt of signal reflections 46 having 90 degree rotated linearly polarized light from that of the emitted linearly polarized light would be analyzed.

Figure 2:
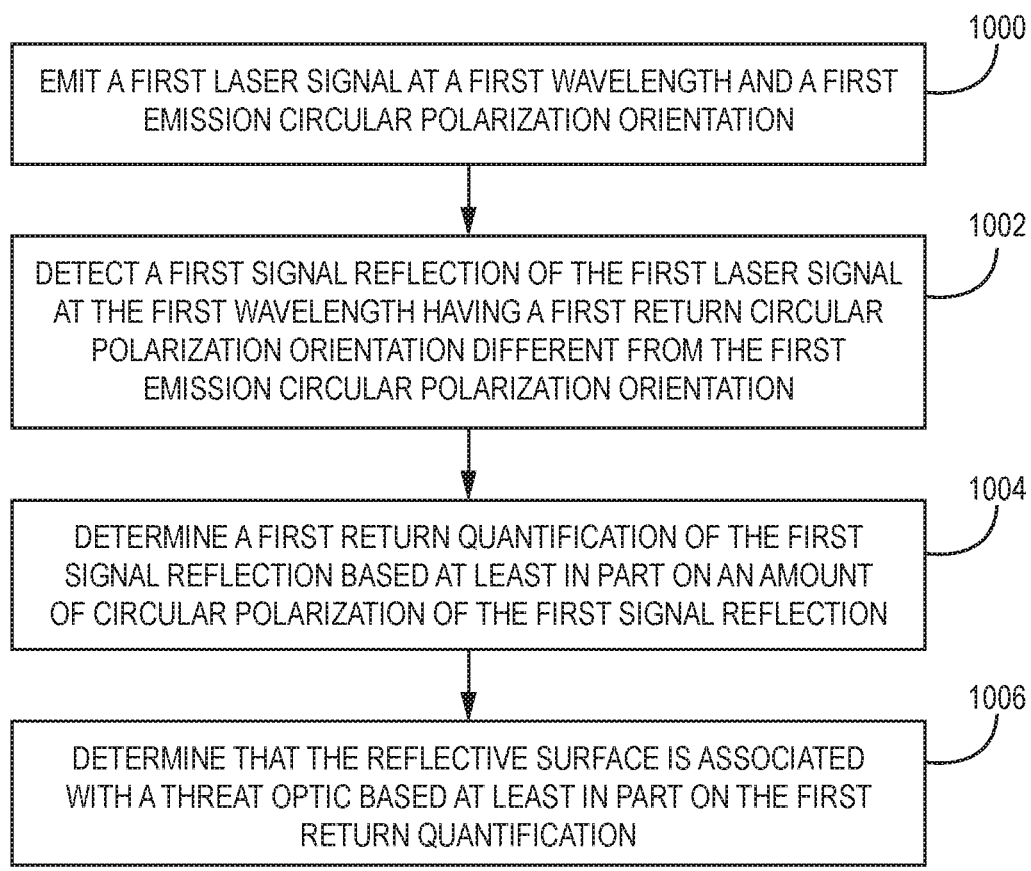
FIG. 2 is a flowchart of a method for distinguishing a threat optic according to one embodiment.

FIG. 2 is a flowchart of a method for distinguishing a threat optic according to one embodiment. FIG. 2 will be discussed in conjunction with FIG. 1. For purposes of illustration, assume that the first laser system 14 emits the laser signal 44-C at a first wavelength and a first emission circular polarization orientation (FIG. 2, block 1000). For example, the first emission circular polarization orientation may be a right hand circular polarization orientation. The laser signal 44-C strikes the object 48-3 in the scene 20. The first detection system 24 detects the signal reflection 46-C of the laser signal 44-C at the first wavelength having a first return circular polarization orientation different from the first emission circular polarization orientation (FIG. 2, block 1002). For example, the first return circular polarization orientation may be a left hand circular polarization orientation. The computing device 30 determines a first return quantification of the first signal reflection 46-C based at least in part on an amount of circular polarization of the first signal reflection 46-C (FIG. 2, block 1004). The computing device 30 determines that the object 48-3 is a threat optic based at least in part on the first return quantification.

Figure 3:
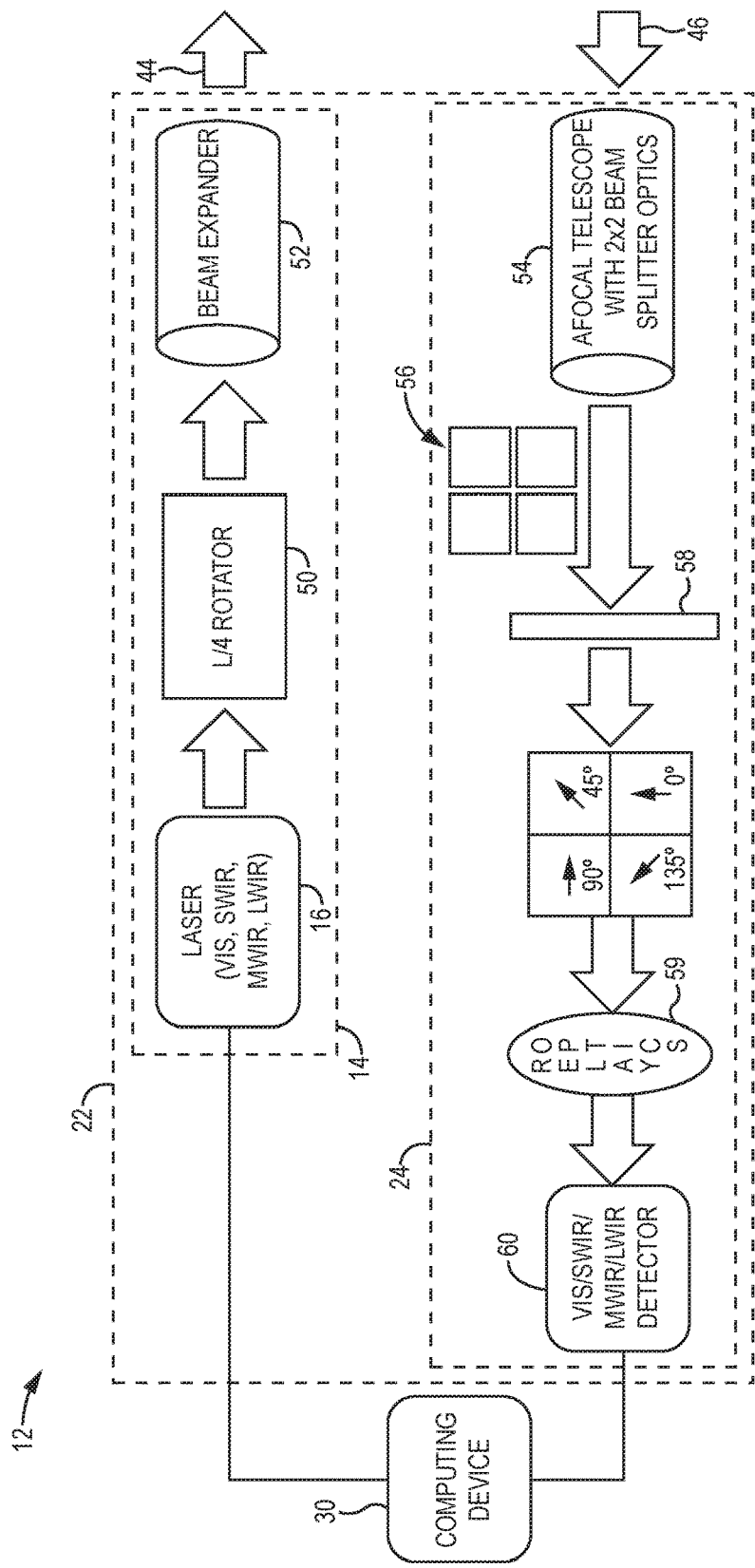
FIG. 3 is a block diagram illustrating aspects of the system illustrated in FIG. 1 in greater detail according to one embodiment.

FIG. 3 is a block diagram illustrating aspects of the system 12 in greater detail according to one embodiment. In this embodiment, the laser system 14 initially emits a linearly polarized laser signal 44 and includes a quarter wave-plate 50 ("L/4") that converts the laser signal 44 emitted by the first laser transmitter 16 into circularly polarized light. A beam expander 52 collimates the laser signal 44 and increases a diameter of the laser signal 44.

The first detection system 24 includes an afocal telescope 54 with a 2×2 beam splitter optical arrangement that receives the signal reflections 46 and splits the signal reflections 46 into four separate but identical channels, or beams 56. The beams 56 pass through a ¼ waveplate and filter array arrangement 58. The ¼ waveplate converts each beam 56 from circularly polarized light to linearly polarized light. The filter array arrangement 58 comprises four polarizers that are oriented at four different orientation positions that allow light that is linearly polarized at a particular angle to pass through and that block light that is linearly polarized at an orthogonal angle. In one embodiment, the four polarizers are rotated at orientation positions of 0, 45, 90, and 135 degrees. The ratio of the amount of light polarized at 0, 45, 90, and 135 degrees determines the amount of circular polarization of the light. The beams 56 are then focused by relay optics 59 onto a detector array 60, such as an infrared focal plane array, or a ultraviolet/visible CMOS or CCD detector array.

The computing device 30 can then analyze the output of the detector array 60 to determine the ratio of the amount of light polarized at 0, 45, 90, and 135 degrees to determine the amount of circular polarization of the light, and thereby generate a return quantification of the signal reflections 46.

Figure 4:
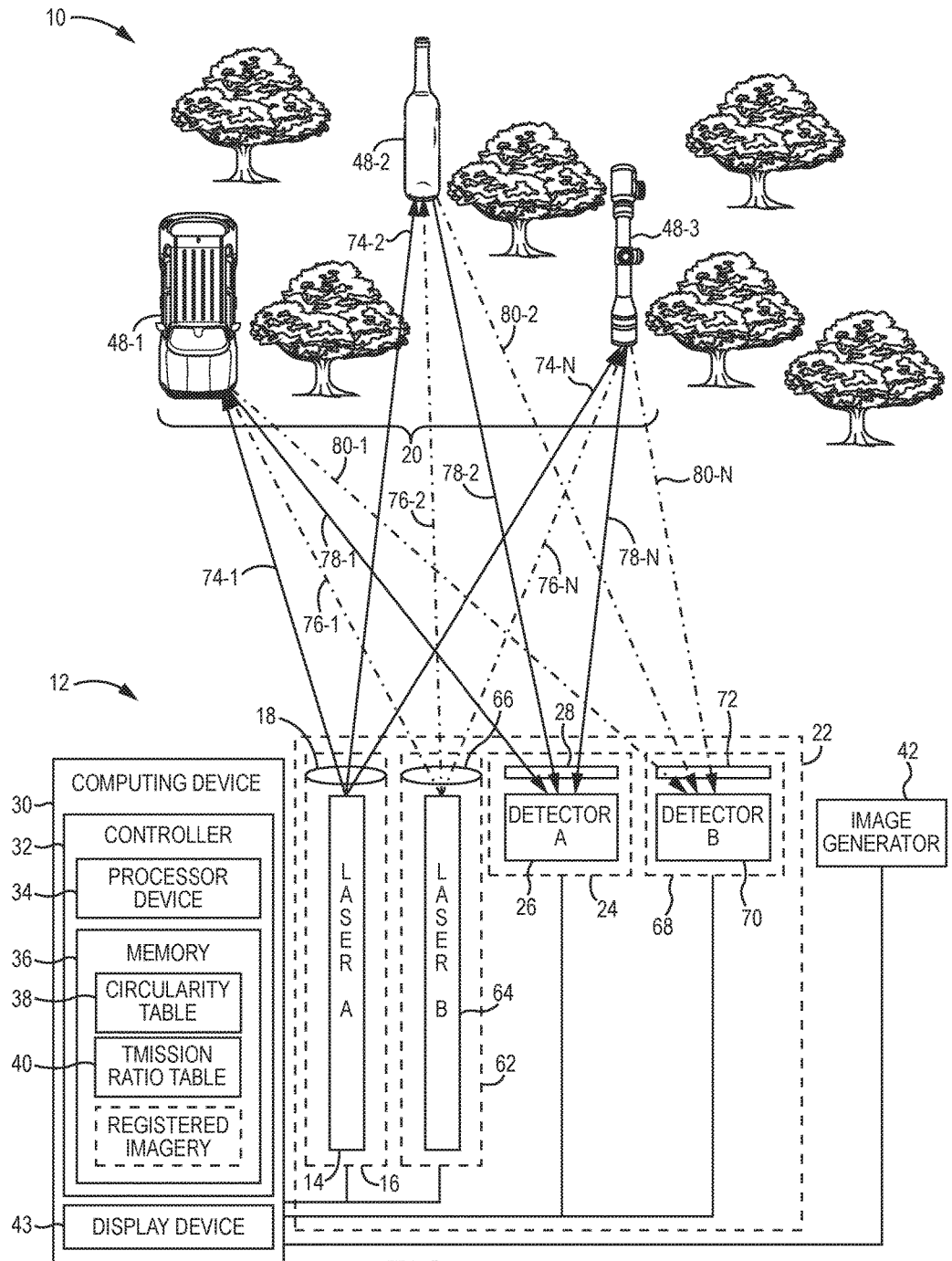
FIG. 4 is a block diagram of the environment illustrated in FIG. 1 with a system according to another embodiment.

FIG. 4 is a block diagram of the environment 10 illustrated in FIG. 1 with a system 12-1 according to another embodiment. The system 12-1 is substantially similar to the system 12 except as otherwise discussed herein. In particular, the system 12-1, as will be discussed in greater detail below, not only distinguishes a threat optic from non-threat optics, as discussed above with regard to the system 12, but also identifies a likely composition of the threat optic. Knowing the composition of the threat optic may facilitate the exact identification of the threat optic, such as a rifle scope or a video camera.

The transmission characteristics of optical elements depend in part on the composition of the optical element and the wavelength of light incident on the optical element. By transmitting laser signals at different wavelengths and measuring the signal reflection, it is possible to determine the particular composition of the optical elements through which the laser signals traveled.

Generally, the embodiments utilize predetermined knowledge about the transmission properties of various compositions of optical elements, along with predetermined knowledge of the reflective characteristics of polarized light, to identify a composition of such optical elements. Among other advantages, the disclosed mechanisms greatly reduce the false identification of reflective surfaces that do not comprise optical elements.

The system 12-1, in addition to the elements discussed above with regard to FIGS. 1-3, also includes a second laser system 62 that includes a second laser transmitter 64 and, in this embodiment, an optical element 66, such as a left hand quarter wave plate that left hand circularly polarizes laser signals emitted from the second laser transmitter 64.

The system 12-1 includes a second detection system 68 that includes a second detector 70 sensitive to laser signals in the same wavelength as the laser signals generated by the second laser transmitter 64. In this embodiment, the second detection system 68 also includes a right hand circular polarizer filter 72 that filters out light that has a polarization orientation other than a right hand circular polarization orientation. In other words, the right hand circular polarizer filter 72 passes right hand circularly polarized light to the second detector 70 and blocks all other light. The second detection system 68 may also include a wavelength filter that blocks wavelengths other than the wavelength of the laser signal emitted by the second laser transmitter 64.

In this example, assume that the first laser system 14 emits laser signals 74-1-74-N at a first laser wavelength and a first laser polarization orientation and that the second laser system 62 emits laser signals 76-1-76-N at a second laser wavelength and a second laser polarization orientation. The first laser wavelength in this example is 10.6 micrometers, and the first laser polarization orientation is a right hand circular polarization orientation. The second laser wavelength in this example is 1550 nanometers, and the second laser polarization orientation is a left hand circular polarization orientation. Note that while in this example both the wavelengths and the polarization orientations differ, in other embodiments, the wavelengths may be the same while the polarization orientations may differ, and in yet other embodiments, the polarization orientations may be identical while the wavelengths may differ. Moreover, while for purposes of illustration only two laser systems 14, 62 are illustrated, the embodiments may use any number of laser systems, such as 4, 5, 6, or more laser systems, of various wavelengths and various polarization orientations for purposes of identifying threat optics in a scene.

In some embodiments, the laser systems 14, 62 may emit pulsed laser signals and time-gate the receipt of reflections of such laser signals to determine range and return levels and/or strength. The laser systems 14, 62 may scan in both elevation and azimuth to identify optical elements throughout the scene 20.

The laser signal 74-1 strikes a headlamp reflective surface of the object 48-1 (i.e., a vehicle) and generates a laser signal reflection 78-1. Because the handedness of a circularly polarized signal changes upon reflection of a surface at normal incidence, the laser signal reflection 78-1 has a left hand circular polarization state. However, because of the characteristics of the headlamp reflective surface, much of the laser signal 74-1 will be dispersed, and the laser signal reflection 78-1 may no longer be circularly polarized. The first detection system 24 receives the laser signal reflection 78-1 and can quantify both the strength of the laser signal reflection 78-1 as well as the amount of circular polarization retained.

Similarly, the laser signal 76-1 strikes the headlamp reflective surface of the object 48-1 and generates the laser signal reflection 80-1. Because the handedness of a circularly polarized signal changes upon reflection of a surface at normal incidence, the laser signal reflection 80-1 has a right hand circular polarization state. However, because of the characteristics of the headlamp reflective surface, much of the laser signal 76-1 will be dispersed, and the laser signal reflection 80-1 may no longer be circularly polarized. The second detection system 68 receives the laser signal reflection 80-1 and can quantify both the strength of the laser signal reflection 80-1 as well as the amount of circular polarization retained. Due to the return quantification of the laser signal reflection 78-1 and the return quantification of the laser signal reflection 80-1, the computing device 30 may determine that the reflective surface is not an optical element. Similar processing may occur with respect to a reflective surface of the reflective object 48-2 (i.e., a bottle).

The laser signal 74-N travels down the column of the object 48-3 (i.e., a rifle scope), strikes a reflective surface, such as a focal plane array, and reflects back through the optical elements of the object 48-3 as a laser signal reflection 78-N. The computing device 30 determines a first return quantification based on the laser signal reflection 78-N. Similarly, the laser signal 76-N travels down the column of the object 48-3, strikes the focal plane array, and reflects back through the optical elements of the object 48-3 as a laser signal reflection 80-N. The computing device 30 determines a second return quantification based on the laser signal reflection 80-N. The computing device 30 compares the first return quantification to the second return quantification and, based on comparing the first return quantification to the second return quantification, determines that the object 48-3 is a threat optic.

In one embodiment, the computing device 30 compares the first return quantification to the second return quantification to determine a transmission ratio and accesses, from the memory 36, a transmission ratio table 82. The transmission ratio table 82 identifies a plurality of different predetermined transmission ratios. The computing device 30 identifies a particular predetermined transmission ratio based on the determined transmission ratio of the first return quantification and the second return quantification. An example of the transmission ratio table 82 according to one embodiment is illustrated below.

| Transmission Ratio Table 82 | | | |
|---|---|---|---|
| | Laser Line T % | | |
| Optical Material | 1550 nm (right handed) | 10.6 um (left handed) | Transmission ratio (signed) |
| Si | 50% | 20% | 2.5 |
| SiO2 | 90% | 0% | >(+)100 |
| Ge | 0% | 40% | >(-)100 |
| ZnSe | 60% | 60% | 1 |

The transmission ratio table 82 may comprise any suitable number of entries and be based on any desired information, such as return level and the like. The transmission ratio table 82 may be developed through experimentation by measuring signal reflections through various threat optics of various materials at various wavelengths.

The measurements of the laser signal reflections 78-N, 80-N may include, for example, relative intensities of the reflected radiation at different wavelengths. In some embodiments, the measurements may be at different polarization orientations, including but not limited to the measurements of 0 degrees, 45 degrees, 90 degrees, 135 degrees. The circular polarization orientation may also be measured opposite to that of the transmitted polarization orientation, as discussed above with regard to FIGS. 1-3. Such measurements may include a complete set of measurements to obtain a Mueller matrix of the light reflecting from the surface of the material. Different metrics of the reflected intensities may be computed at different wavelengths and polarization orientations. Such metrics may be relatively simple ratios of the same or different polarization orientations at different wavelengths, ratios of weighted linear combinations thereof, or ratios of more complex functions of wavelength and polarization orientations. Such metrics enable the characterization of the polarization properties of the reflecting objects 48 and thereby permit inferences as to the characteristics of the reflecting materials, including, for example, dielectric, metal, natural, manmade, and the like. Such metrics may be useful to differentiating remote optical elements from natural and manmade clutter.

Figure 5:
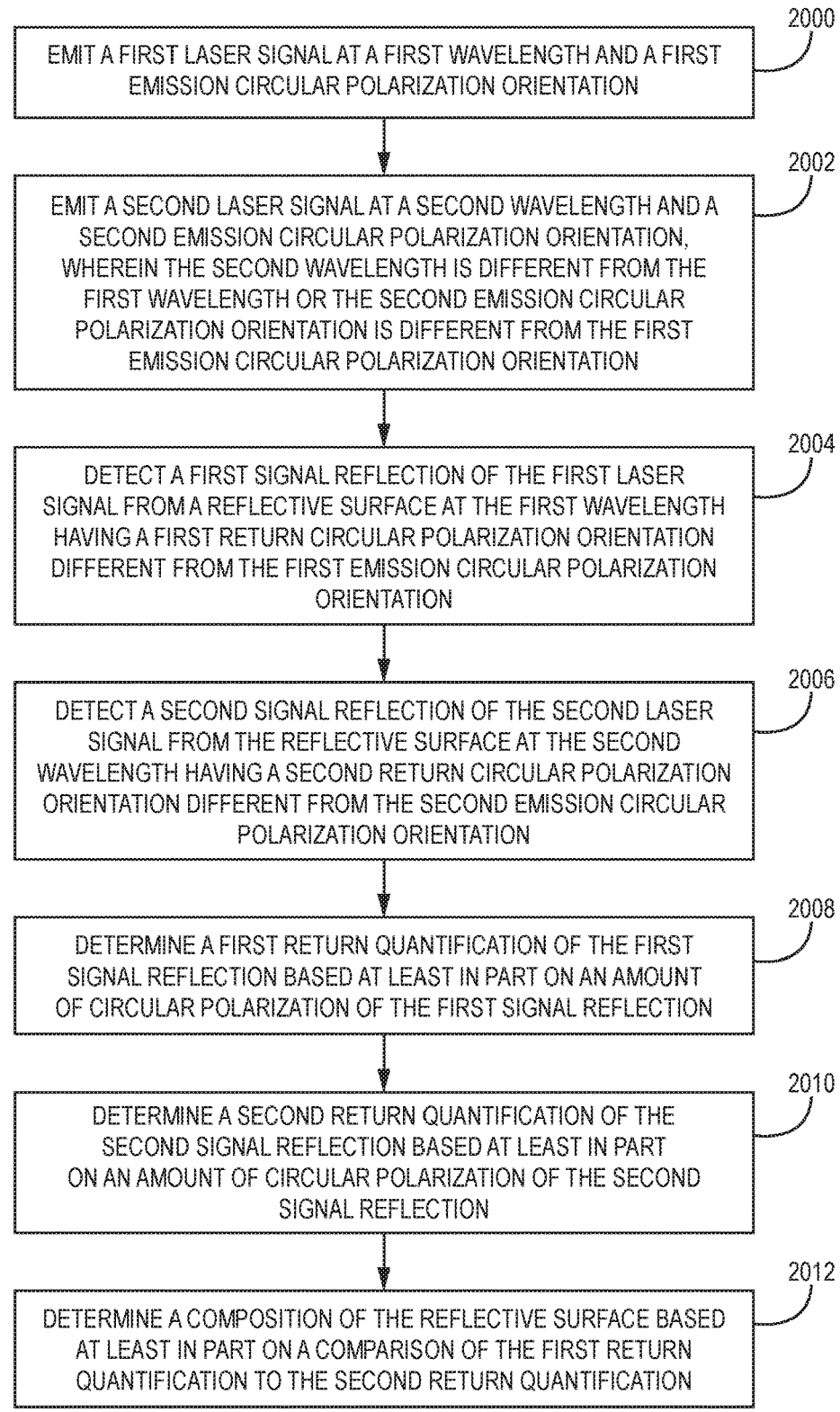
FIG. 5 is a flowchart of a method for identifying a composition of a threat optic according to one embodiment.

FIG. 5 is a flowchart of a method for identifying a composition of a threat optic according to one embodiment. FIG. 5 will be discussed in conjunction with FIG. 4. The first laser system 14 emits the first laser signal 74-N at a first laser wavelength and a first emission circular polarization orientation (FIG. 5, block 2000). The second laser system 62 emits the second laser signal 76-N at a second laser wavelength and a second emission circular polarization orientation, wherein the second wavelength is different from the first wavelength and/or the second emission circular polarization orientation is different from the first emission circular polarization orientation (FIG. 5, block 2002). The second detection system 68 detects the second laser signal reflection 80-N of the second laser signal 76-N from the reflective object 48-3 (FIG. 5, block 2006). The first detection system 24 detects a first laser signal reflection 78-N of the first laser signal 74-N from the reflective object 48-3 (FIG. 5, block 2004). The controller 32 determines a first return quantification based on the first laser signal reflection 78-N (FIG. 5, block 2008). The controller 32 determines a second return quantification based on the second laser signal reflection 80-N (FIG. 5, block 2010). The controller 32 compares the first return quantification to the second return quantification and, based on comparing the first return quantification to the second return quantification, determines a composition of the reflective object 48-3 (FIG. 5, block 2012).

Figure 6:
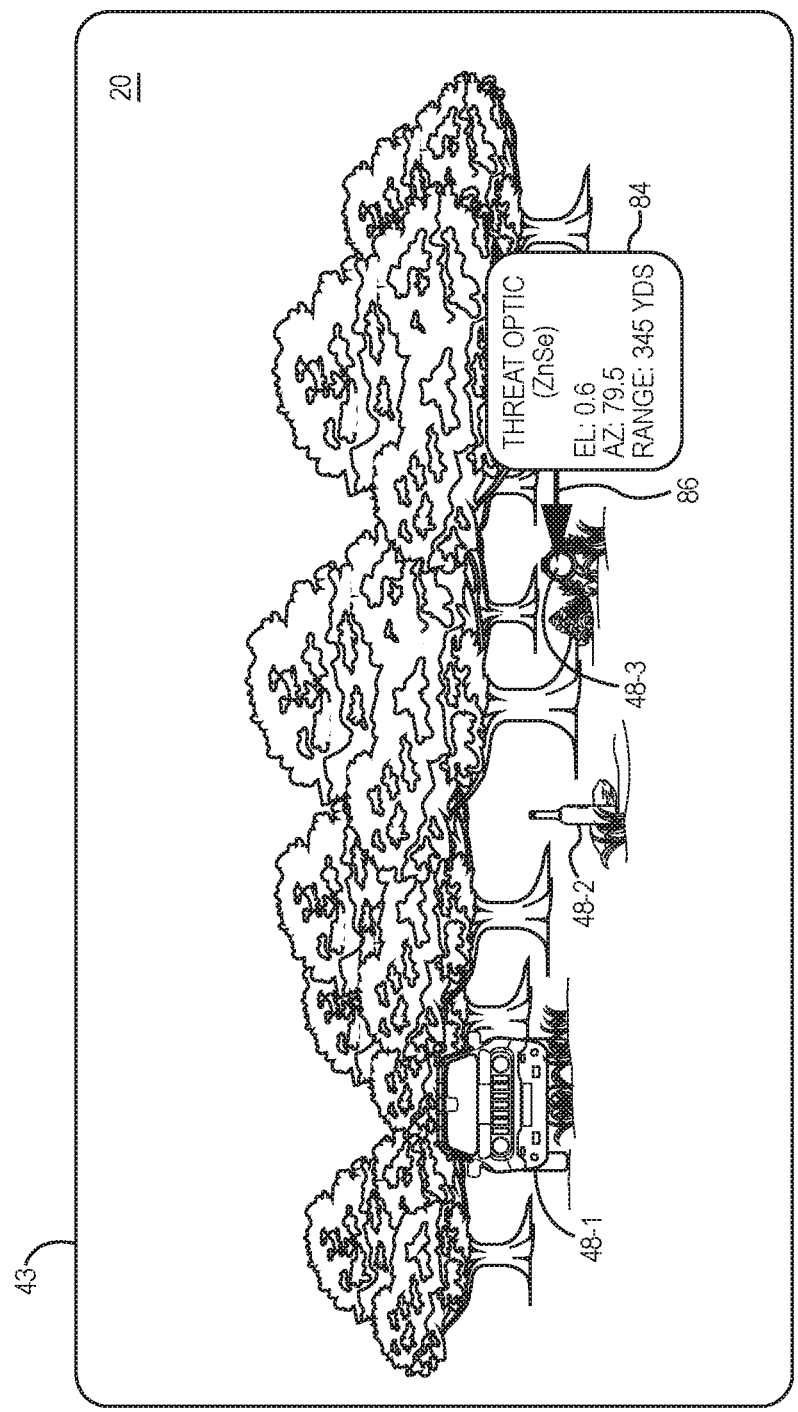
FIG. 6 is a diagram of a display device according to one embodiment.

FIG. 6 is a diagram of the display device 43 according to one embodiment. FIG. 6 illustrates an example of what may be presented to a user of the systems 12, 12-1 according to one embodiment. In this example, the system 12 superimposes a window 84 that provides data determined by the system 12 based on the process described above with regard to FIG. 5. The system 12 also superimposes an arrow 86 pointing to a precise of location of the identified threat optic in the scene 20. The window 84 identifies a composition of the threat optic as ZnSe, and identifies a location of the threat optic in terms of elevation and azimuth and a range to the threat optic.

Those skilled in the art will recognize improvements and modifications to the preferred embodiments of the disclosure. All such improvements and modifications are considered within the scope of the concepts disclosed herein and the claims that follow.

What is claimed is:

1. A method for identifying a threat optic in a scene comprising:

emitting, from a first laser system, a first laser signal at a first wavelength and a first emission circular polarization orientation;

converting, into linearly polarized light via a wave plate, a first signal reflection of the first laser signal from a reflective surface at the first wavelength;

passing the linearly polarized light through a plurality of polarizers oriented at different orientation positions;

detecting the linearly polarized light passed through the plurality of polarizers;

determining a first return quantification of the first signal reflection based at least in part on an amount of circularity of polarization of the first signal reflection by:

determining a ratio of light received at the different orientation positions; and
determining the amount of circularity of polarization of the first signal reflection based on the ratio; and
determining whether the reflective surface is associated with a threat optic based at least in part on the first return quantification.

2. The method of claim 1 wherein
the wave plate comprises a ¼ wave plate;
and wherein the plurality of polarizers comprises four polarizers oriented at four different orientation positions.

3. The method of claim 2 wherein the different orientation positions comprise a 0 degree position, a 45 degree position, a 90 degree position, and a 135 degree position.

4. The method of claim 1 further comprising:
emitting, from a second laser system, a second laser signal at a second wavelength and a second emission circular polarization orientation, wherein the second wavelength is different from the first wavelength or the second emission circular polarization orientation is different from the first emission circular polarization orientation;
detecting a second signal reflection of the second laser signal from the reflective surface at the second wavelength having a second return circular polarization orientation different from the second emission circular polarization orientation;
determining a second return quantification of the second signal reflection based at least in part on an amount of circular polarization of the second signal reflection; and
determining a composition of the threat optic based at least in part on a comparison of the first return quantification to the second return quantification.

5. The method of claim 4, wherein the second emission circular polarization orientation is different from the first emission circular polarization orientation.

6. The method of claim 4, wherein determining the composition of the threat optic based at least in part on the comparison of the first return quantification to the second return quantification further comprises:
comparing the first return quantification to the second return quantification to determine a transmission ratio;
accessing, from a memory, a transmission ratio table that identifies a plurality of different predetermined transmission ratios; and
determining that the transmission ratio matches a particular predetermined transmission ratio of the plurality of different predetermined transmission ratios.

7. The method of claim 6, wherein each predetermined transmission ratio of the plurality of different predetermined transmission ratios corresponds to a particular optical element composition; and
further comprising identifying a particular optical element composition that corresponds to the particular predetermined transmission ratio.

8. The method of claim 1, further comprising identifying a location of the threat optic with respect to imagery of the scene.

9. The method of claim 8, further comprising:
presenting, on a display device, the imagery of the scene; and
identifying, in the imagery, the location of the threat optic.

10. The method of claim 9, further comprising identifying, in the imagery, a composition of the threat optic.

11. The method of claim 9, further comprising identifying the location of the threat optic in the imagery of the scene by elevation, azimuth, and/or range.

12. A system comprising:
a first laser system configured to emit a first laser signal at a first wavelength and a first emission circular polarization orientation;
a wave plate configured to convert into linearly polarized light a first signal reflection of the first laser signal from a reflective surface at the first wavelength;
a plurality of polarizers configured to be oriented at different orientation positions and to pass the linearly polarized light in a downstream direction;
a first detector configured to receive the linearly polarized light from the plurality of polarizers;
a processor device configured to:
determine a first return quantification of the first signal reflection based at least in part on an amount of circularity of polarization of the first signal reflection by:
determining a ratio of light received at the different orientation positions; and
determining the amount of circularity of polarization of the first signal reflection based on the ratio; and
determine whether the reflective surface is associated with a threat optic based at least in part on the first return quantification.

13. The system of claim 12 wherein the wave plate comprises
a ¼ wave plate; and wherein the plurality of polarizers comprises
four polarizers configured to be oriented at four different orientation positions.

14. The system of claim 13 wherein the different orientation positions comprise a 0 degree position, a 45 degree position, a 90 degree position and a 135 degree position.

15. The system of claim 12 further comprising:
a second laser system configured to emit a second laser signal at a second wavelength and a second emission circular polarization orientation, wherein the second wavelength is different from the first wavelength or the second emission circular polarization orientation is different from the first emission circular polarization orientation; and
a second detector configured to detect a second signal reflection of the second laser signal from the reflective surface at the second wavelength having a second return circular polarization orientation different from the second emission circular polarization orientation; and
wherein the processor device is further configured to:
determine a second return quantification of the second signal reflection based at least in part on an amount of circular polarization of the second signal reflection; and
determine a composition of the threat optic based at least in part on a comparison of the first return quantification to the second return quantification.

16. The system of claim 15, wherein the second emission circular polarization orientation is different from the first emission circular polarization orientation.

17. The system of claim 15, wherein to determine the composition of the threat optic based at least in part on the comparison of the first return quantification to the second return quantification the processor device is further configured to:

compare the first return quantification to the second return quantification to determine a transmission ratio;

access, from a memory, a transmission ratio table that identifies a plurality of different predetermined transmission ratios; and determine that the transmission ratio matches a particular predetermined transmission ratio of the plurality of different predetermined transmission ratios.

18. The system of claim 17, wherein each predetermined transmission ratio of the plurality of different predetermined transmission ratios corresponds to a particular optical element composition, and wherein the processor device is further configured to identify a particular optical element composition that corresponds to the particular predetermined transmission ratio.

19. The system of claim 12, further comprising identifying a location of the threat optic with respect to imagery of the scene.

20. The system of claim 19, wherein the processor device is further configured to:
present, on a display device, the imagery of the scene; and
identify, in the imagery, the location of the threat optic.

21. A method for identifying a threat optic in a scene, comprising:
emitting, from a first laser system, a first laser signal at a first wavelength and a first emission circular polarization orientation;

detecting a first signal reflection of the first laser signal from a reflective surface at the first wavelength;

determining a first return quantification of the first signal reflection based at least in part on an amount of circular polarization of the first signal reflection;

determining that the reflective surface is associated with a threat optic based at least in part on the first return quantification;

emitting, from a second laser system, a second laser signal at a second wavelength and a second emission circular polarization orientation, wherein the second wavelength is different from the first wavelength or the second emission circular polarization orientation is different from the first emission circular polarization orientation;

detecting a second signal reflection of the second laser signal from the reflective surface at the second wavelength having a second return circular polarization orientation different from the second emission circular polarization orientation;

determining a second return quantification of the second signal reflection based at least in part on an amount of circular polarization of the second signal reflection; and determining a composition of the threat optic based at least in part on a comparison of the first return quantification to the second return quantification.

* * * * *